(12) United States Patent
Kleiner

(10) Patent No.: US 6,303,674 B1
(45) Date of Patent: Oct. 16, 2001

(54) ALUMINIUM SALTS OF ALKYLHYDROXYMETHYLPHOSPHINIC ACIDS

(75) Inventor: Hans-Jerg Kleiner, Kronberg (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/380,669

(22) PCT Filed: Feb. 19, 1998

(86) PCT No.: PCT/EP98/00947

§ 371 Date: Dec. 6, 1999

§ 102(e) Date: Dec. 6, 1999

(87) PCT Pub. No.: WO98/39338

PCT Pub. Date: Sep. 11, 1998

(30) Foreign Application Priority Data

Mar. 4, 1997 (DE) ............................................. 197 08 725

(51) Int. Cl.$^7$ .................... C08J 3/20; C07F 9/30
(52) U.S. Cl. ................... 524/133; 524/136; 524/139; 562/23; 556/174; 556/182
(58) Field of Search .................... 524/133, 136, 524/139; 562/23; 556/174, 182

(56) References Cited

U.S. PATENT DOCUMENTS

| | | |
|---|---|---|
| 3,594,347 | 7/1971 | Lazarus et al. . |
| 3,892,998 | 7/1975 | Tsui et al. . |
| 3,900,444 | 8/1975 | Racky et al. . |
| 3,953,539 | 4/1976 | Kawase et al. . |
| 4,036,811 | 7/1977 | Noetzel et al. . |
| 4,049,612 | 9/1977 | Sandler . |
| 4,078,016 | 3/1978 | Kramer . |
| 4,180,495 | 12/1979 | Sandler . |
| 4,208,321 | 6/1980 | Sandler . |
| 4,208,322 | 6/1980 | Sandler . |
| 5,196,554 * | 3/1993 | Svara ....................................... 556/13 |
| 5,780,534 | 7/1998 | Kleiner et al. . |

FOREIGN PATENT DOCUMENTS

| | | |
|---|---|---|
| 700042 | 7/1967 | (BE) . |
| 2 102 841 | 8/1971 | (DE) . |
| 2 252 256 | 5/1974 | (DE) . |
| 2 252 258 | 5/1974 | (DE) . |
| 2 447 727 | 4/1976 | (DE) . |
| 2 915 116 | 10/1979 | (DE) . |
| 006 568 | 1/1980 | (EP) . |
| 2 827 867 | 1/1980 | (DE) . |
| 452 755 | 10/1991 | (EP) . |
| 458 067 | 11/1991 | (EP) . |
| 699 708 | 3/1996 | (EP) . |
| 794 191 | 9/1997 | (EP) . |
| 2 204 659 | 10/1972 | (FR) . |
| 2 422 698 | 4/1978 | (FR) . |

OTHER PUBLICATIONS

Derwent English Abstract (1971–52012S) for DE 2 102 841 (Aug. 5, 1971).
Derwent English Abstract (1974–C6071V) for DE 2 252 256 (May 9, 1974).
Derwent English Anstract (1974–34563V) for DE 2 252 258 (May 9, 1974).
Derwent English Abstract (1976–28565X) for DE 2 447 727 (Apr. 8, 1976).
Derwent English Abstract (1979–59863B) for DE 2 915 116 (Oct. 25, 1979).
Derwent English Abstract (1980–02156C) for DE 2 827 867 (Jan. 17, 1980).
Derwent English Abstract (1980–02156C) for EP 006 568 (Jan. 9, 1980).
Derwent English Abstract (1991–312047) for EP 452 755 (Oct. 23, 1991).
Derwent English Abstract (1991–347511) for EP 458 067 (Nov. 27, 1991).
Derwent English Abstract (1996–130732) for EP 699 708 (Mar. 6, 1996).
Derwent English Abstract (1997–437433) for EP 794 191 (Sep. 10, 1997).
Derwent English Abstract (1974–34563V) for FR 2 204 659 (Oct. 25, 1972).
Derwent English Abstract (1979–59863B) for FR 2 422 698 (Apr. 13, 1978).
Derwent English Abstract (1976–42858X) for JP 51 047035 and JP 82 059262 (Apr. 22, 1976).
English Abstract for BE 700,042.

* cited by examiner

Primary Examiner—Margaret Medley
Assistant Examiner—Cephia D. Toomer
(74) Attorney, Agent, or Firm—Connolly Bove Lodge & Hutz LLP

(57) ABSTRACT

Aluminum salts of alkylhydroxymethylphosphinic acids are prepared by reacting phosphonous acids with aluminum hydroxide or paraformaldehyde or trioxane or mixtures thereof in water at 110 to 250° C. under pressure. The resulting aluminumphosphinates are incorporated into polymers, in particular into polyesters, and have a flame retardant action therein.

9 Claims, No Drawings

ALUMINIUM SALTS OF ALKYLHYDROXYMETHYLPHOSPHINIC ACIDS

This application is a 371 of PCT/EP98/00947, filed Feb. 19, 1998.

BACKGROUND OF THE INVENTION

1. Field of the Invention

The invention relates to novel aluminum salts of alkylhydroxymethylphosphinic acids, their preparation and their use as flame retardants.

2. Description of the Prior Art

Polymers are frequently made flame retardant by adding to them phosphorus-containing or halogen-containing compounds or mixtures thereof. Some polymers are processed at high temperatures, e.g. at 250° C. or above. For this reason, many known flame retardants are not suitable for such applications, because they are too volatile or are not sufficiently heat-stable.

Alkali metal salts of dialkylphosphinic acids are thermally stable and are already proposed as flame retardant additives for polyester (DE-A1-2 252 258). They must be introduced in amounts of up to 30% by weight and some have an adverse corrosion-promoting effect on the processing machinery.

Furthermore, the salts of dialkylphosphinic acids with an alkali metal or a metal from the second or third main group or subgroup of the Periodic Table of the Elements have been used for the preparation of flame-resistant polyamide molding compounds, in particular the zinc salts (DE-A1-2 447 727). Low-flammability thermoplastics may also be prepared by using said salts of phosphonic acids in combination with nitrogen bases such as melamine, dicyanodiamide or guanidine (DE-A1-28 27 867). A further large class of salts of phosphonic acids are the polymeric metal phosphinates. These are nonionic coordination complexes and are soluble in organic solvents. They are suitable as flame retardant components for halogenated aromatic polymers and for polyesters (U.S. Pat. No. 4,078,016; U.S. Pat. No. 4,180,495), polyamides (U.S. Pat. No. 4,208,321) and polyesters/polyamides (U.S. Pat. No. 4,208,322). The generally difficult industrial preparation of these metal phosphinate polymers is a disadvantage.

Dialkylphosphinic acids are prepared by free-radical catalyzed addition of olefins to monoesters of phosphonous acid and the subsequent hydrolysis of the dialkylphosphinic esters thus produced. The monoesters of phosphonous acid are produced by esterifying the phosphonous acids. The processes are technically complex and proceed via a plurality of stages. Technically simple preparation processes for salts of phosphonic acids are therefore sought.

SUMMARY OF THE INVENTION

The object is achieved by a process for preparing aluminum salts of alkylhydroxymethylphosphinic acids of the formula (I)

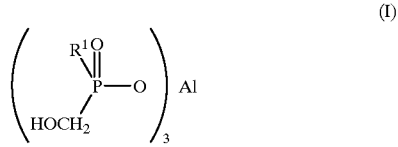

where $R^1$ is an unbranched or branched alkyl radical having 1 to 8 carbon atoms, preferably methyl, ethyl, propyl, butyl or pentyl, which comprises reacting phosphonic acids of the formula (II)

where $R^1$ has the meaning given above with aluminum hydroxide and formaldehyde and/or paraformaldehyde and/or trioxane in water under pressure at 110–250° C.

DESCRIPTION OF THE PREFERRED EMBODIMENTS

It is surprising that in the course of the reaction no decomposition of the phosphonic acids used is observed. This is surprising, in particular, because it is known that aliphatic phosphonic acids convert even below 100° C. in the course of a disproportionation (Methoden der Organischen Chemie [Methods in Organic Chemistry], Houben-Weyl, volume XII/1, page 64, 1963).

As phophinic acids, use is preferably made of methanephosphinic acid, ethanephosphinic acid, butanephosphinic acid or pentanephosphinic acid. Particular reference is given to methanephosphinic acid.

The formaldehyde can be used in aqueous solution. Paraformaldehyde or trioxane can likewise be used in this manner.

The use of solvents other than water is possible. For example, methanol, isopropanol, acetone or acetic acid can be used. However, carrying out the process according to the invention without using other organic solvents is preferred. The process is carried out in such a manner that the phosphonous acid, formaldehyde, aluminum hydroxide in a molar ratio of 3:3:1 in water are heated in an autoclave under pressure at temperatures of 110 to 250° C., preferably 130 to 170° C. After reaction is complete, the mixture is cooled and filtered off with suction. The aluminum salts of the alkylhydroxymethylphosphinic acids are then rigorously dried, preferably under reduced pressure at temperatures of 150 to 200° C. They are then virtually anhydrous and are highly suitable as flame retardants for thermoplastics, e.g. for polyesters such as poly(butylene terephthalate).

Polyesters are polymers which contain repeating units bound via an ester group in the polymer chain. Polyesters which can be used according to the invention are described, for example, in "Ullmann's encyclopedia of industrial chemistry", ed. Barbara Elvers, Vol. A21, Chapter 'Polyesters' (pp. 227–251), VCH, Weinheim-Basle-Cambridge-New York 1992, which is incorporated herein by reference.

The amount of the salt of phosphinic acid of the formula I to be added to the polymers can vary within broad limits. Generally, 5 to 30% by weight are used, based on the polymer. The optimum amount depends on the nature of the polymer and on the type of the salt of phosphinic acid used and can readily be determined by experiments.

The salts of phosphinic acid according to the invention can be used in various physical forms, depending on the type of the polymer used and on the desired properties. Thus, for example to achieve an enhanced dispersion in the polymer, the salts of phosphinic acid can be ground to give a finely particulate form. If desired, mixtures of different salts of phosphinic acid can also be used.

The salts of phosphinic acid according to the invention are thermally stable, and neither decompose the polymers during processing nor affect the production process of the polyester molding composition. The salts of phosphinic acid are not volatile under preparation and processing conditions for polymers.

The salt of phosphinic acid can be incorporated into the polymer by mixing the two and then melting the polymer in a compounding unit (e.g. in a twin-screw extruder) and homogenizing the salt of phosphinic acid in the polymer melt. The melt can be taken off as extrudate, cooled and granulated. The salt of phosphinic acid can also be metered directly into the compounding unit.

It is also possible to admix the flame-retardant additives to finished polyester granules and process the mixture directly on an injection molding machine or to melt the flame-resistant additives in advance in an extruder, to granulate them and process them after a drying process.

The flame-retardant additive can also be added during the polycondensation.

In addition to salts of phosphinic acid according to the invention, fillers and reinforcing agents such as glass fibers, glass beads or minerals such as chalk can be added to the formulations. In addition, the product can comprise other additives, such as stabilizers, lubricants, colorants, nucleating agents or antistatics.

The low-flammability polyesters according to the invention are suitable for the preparation of shaped bodies, films, filaments and fibers, e.g. by injection molding, extrusion or pressing.

EXAMPLE 1

Preparation of the Aluminum Salt of Hydroxymethylmethylphosphinic Acid Using Paraformaldehyde 728 g (9.1 mol) of methanephosphonous acid, 237 g (3.03 mol) of aluminum hydroxide, 273 g (9.1 mol) of paraformaldehyde and 1440 g of water were charged into a 5 l V4A autoclave equipped with a blade agitator and kept at 150° C. for 48 hours. In the course of this the pressure increased to 3.5 to 4 bar. The mixture was then cooled, filtered off with suction, washed with a sparing amount of water and dried at 150° C. in a vacuum drying cabinet. 750 g of aluminum salt of hydroxymethylmethylphosphinic acid having a melting point above 360° C. were obtained. This corresponds to a yield of 70% of theory Result of elemental analysis: $C_6H_{18}AlO_9P_3$ (354)

| calculated: | 20.3% C | 5.08% H | 26.3% P | 7.63% Al |
|---|---|---|---|---|
| found: | 18.5% C | 5.20% H | 25.6% P | 8.80% Al |

EXAMPLE 2

Preparation of the Aluminum Salt of Hydroxymethylmethylphosphinic Acid Using Formalin Solution 360 g (4.5 mol) of methanephosphonous acid, 117 g (1.5 mol) of aluminum hydroxide, 365 g (4.5 mol) of 37% strength formalin solution and 671 g of water were kept at 140° C. in a 2 l autoclave for 48 hours. The mixture was then cooled, filtered off with suction, washed and dried at 140° C. in a vacuum drying cabinet. 266 g of aluminum salt of hydroxymethylmethylphosphinic acid were obtained. The filtrate was substantially freed from water under reduced pressure and the residue was digested with methanol. The mixture was then filtered off with suction, washed and dried at 140° C. in a vacuum drying cabinet. A further 121 g were obtained, that is in total 387 g of aluminum salt of hydroxymethylmethylphosphinic acid. This corresponds to a yield of 73% of theory.

EXAMPLE 3

From the aluminum salt of hydroxymethylmethylphosphinic acid, prepared as in Example 1, and poly(butylene terephthalate), compounds were produced, reinforced with 30% glass fibers, without further additives, test pieces of thickness 0.8 mm were extruded and tested with the following result:

| Concentration % | Flammability rating UL94 | Stress at break N/mm$^2$ | Elongation at break % | Modulus of elasticity N/mm$^2$ |
|---|---|---|---|---|
| 20 | V2 | 107.3 | 1.8 | 10211 |

Test pieces without the addition of 30% glass fibers likewise achieved the flammability rating V2 containing 20% aluminum salt.

What is claimed is:

1. A process for preparing the aluminum salt of an alkylhydroxymethylphosphinic acid of the formula (I):

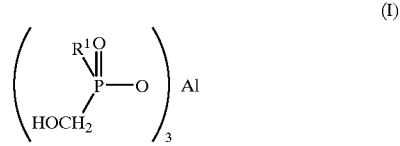

where $R^1$ is an alkyl group having 1 to 8 carbon atoms which comprises reacting a phosphinic acid of the formula (II):

where $R^1$ is defined as in formula (I), with aluminum hydroxide and, at least one of formaldehyde, paraformaldehyde and trioxane, at a temperature of from 110 to 250° C., and under a pressure.

2. The process as claimed in claim 1, wherein the phosphinic acid to aluminum hydroxide to at least one of formaldehyde, paraformaldehyde and trioxane are present in a ratio of 3:1:3.

3. The process as claimed in claim 1, wherein the temperature is from 130 to 170° C.

4. The process as claimed in claim 1, wherein $R^1$ is a methyl, ethyl, propyl, butyl or pentyl group.

5. The process as claimed in claim 1, wherein the at least one of formaldehyde, paraformaldehyde and trioxane is in an aqueous solution.

6. The process as claimed in claim 1, wherein the reaction is carried out in a solvent.

7. The process as claimed in claim 6, wherein the solvent is water.

8. The process as claimed in claim 6, wherein the solvent is organic.

9. The process as claimed in claim 8, wherein the organic solvent is methanol, isopropanol, acetone or acetic acid.

* * * * *